US010806391B2

(12) United States Patent
Panicker et al.

(10) Patent No.: US 10,806,391 B2
(45) Date of Patent: Oct. 20, 2020

(54) METHOD AND SYSTEM FOR MEASURING A VOLUME OF AN ORGAN OF INTEREST

(71) Applicant: General Electric Company, Schenectady, NY (US)

(72) Inventors: Mahesh R. Panicker, Bangalore (IN); Sigmund Frigstad, Trondheim (NO); Pavan Kumar V Annangi, Bangalore (IN); Srinivas Varna, Bangalore (IN); Abhijit Vishwas Patil, Bangalore (IN); Anders Herman Torp, Oslo (NO)

(73) Assignee: General Electric Company, Schenectady, NY (US)

( * ) Notice: Subject to any disclaimer, the term of this patent is extended or adjusted under 35 U.S.C. 154(b) by 421 days.

(21) Appl. No.: 15/703,377

(22) Filed: Sep. 13, 2017

(65) Prior Publication Data

US 2018/0085043 A1 Mar. 29, 2018

(30) Foreign Application Priority Data

Sep. 26, 2016 (IN) .............................. 201641032721

(51) Int. Cl.
*A61B 5/20* (2006.01)
*A61B 8/08* (2006.01)
(Continued)

(52) U.S. Cl.
CPC ............ *A61B 5/204* (2013.01); *A61B 5/4238* (2013.01); *A61B 8/0858* (2013.01);
(Continued)

(58) Field of Classification Search
CPC ........... G06T 7/62; G06T 7/50; G06T 7/0012; G06T 2207/10132; G06T 2207/30004; A61B 5/204; A61B 5/4238; A61B 5/1073; A61B 5/1075; A61B 8/0858; A61B 8/4254; A61B 8/4427; A61B 8/466; A61B 8/485; A61B 8/486; A61B 8/488; A61B 8/5207
See application file for complete search history.

(56) References Cited

U.S. PATENT DOCUMENTS 6,193,660 B1 * 2/2001 Jackson ................... A61B 8/00
600/443
2005/0228278 A1 * 10/2005 Chalana ............... A61B 8/0858
600/437

(Continued)

*Primary Examiner* — Carolyn A Pehlke

(57) ABSTRACT

In an embodiment of the subject matter described herein a system is provided. The system includes a portable host system having one or more processors and a memory for storing a plurality of applications. The one or more processors configured to execute programmed instructions of a select application by performing one or more operations, which include obtain a set of frames of 2D ultrasound images, develop a prospect model indicating a likelihood that frames within the set include an organ of interest (OOI), identify primary and secondary reference frames from the set of the frames based on the prospect model, determine a characteristic of interest in the primary reference frame, select a candidate shape for the OOI based on the character of interest in the primary reference frame, and adjust the candidate shape based on the secondary reference frames to form a resultant shape for the OOI.

18 Claims, 11 Drawing Sheets

(51) Int. Cl.
*G06T 7/00* (2017.01)
*G06T 7/62* (2017.01)
*G06T 7/50* (2017.01)
*A61B 5/00* (2006.01)
*A61B 8/00* (2006.01)
*A61B 5/107* (2006.01)

(52) U.S. Cl.
CPC .......... *A61B 8/4254* (2013.01); *A61B 8/4427* (2013.01); *A61B 8/466* (2013.01); *A61B 8/485* (2013.01); *A61B 8/486* (2013.01); *A61B 8/488* (2013.01); *A61B 8/5207* (2013.01); *G06T 7/0012* (2013.01); *G06T 7/50* (2017.01); *G06T 7/62* (2017.01); *A61B 5/1073* (2013.01); *A61B 5/1075* (2013.01); *A61B 8/085* (2013.01); *A61B 8/4472* (2013.01); *A61B 8/48* (2013.01); *G06T 2207/10132* (2013.01); *G06T 2207/30004* (2013.01); *G06T 2207/30056* (2013.01); *G06T 2207/30084* (2013.01)

(56) References Cited

U.S. PATENT DOCUMENTS

2016/0300343 A1* 10/2016 Gazit ...................... G16H 50/50
2017/0164924 A1* 6/2017 Urabe ................. A61B 5/1075

* cited by examiner

US 10,806,391 B2

METHOD AND SYSTEM FOR MEASURING A VOLUME OF AN ORGAN OF INTEREST

BACKGROUND OF THE INVENTION

The subject matter disclosed herein relates generally to ultrasound imaging systems, and more particularly, to a method and apparatus for performing volume measurements using a mobile ultrasound imaging system of an organ of interest.

Ultrasound imaging systems typically include ultrasound scanning devices, such as, ultrasound probes having different transducers that allow for performing various different ultrasound scans (e.g., different imaging of a volume or body). Mobile or pocket sized ultrasound imaging systems are gaining significance due to their portability, low costs, and no compromise on image quality. Mobile ultrasound imaging systems may be utilized to perform various procedures that were once only accomplished in a dedicated medical facility, for example, a hospital. Mobile ultrasound imaging systems can include diagnostic tools based on acquired ultrasound images of the ultrasound imaging system. Some diagnostic tools can determine a volume of an organ of interest by the clinician, such as the bladder. The volume of an organ of interest can be used to diagnose a number of clinical conditions requiring treatment. For example, the differences between a pre-void and post-void volume of the bladder may be used for a urinary retention diagnosis.

However, currently available volume diagnostic tools for mobile ultrasound imaging system use manual volume measurements. Manual volume measurements are time consuming requiring the clinician to identify edges and dimensions of the organ of interest from one or more ultrasound images. For example, the user must acquire longitudinal and transverse B-mode images and measure the region of interest by manually positioning calipers to determine a volume of the organ of interest. Further, due to the small screens and limited space for user interface components, the user interaction with the conventional mobile ultrasound imaging systems are limited and do not provide assistance for protocol or step guidance for volume diagnostic tools.

BRIEF DESCRIPTION OF THE INVENTION

In an embodiment a method is provided. The method includes obtaining a set of frames of 2D ultrasound images. The method further includes using one or more processors to develop a prospect model indicating a likelihood that frames within the set include an organ of interest (OOI), identify primary and secondary reference frames from the set of the frames based on the prospect model, and determine a characteristic of interest in the primary reference frame. The method further using the one or more processors to select a candidate shape for the OOI based on the character of interest in the primary reference frame, and adjust the candidate shape based on the secondary reference frames to form a resultant shape for the OOI.

In an embodiment a system (e.g., a mobile ultrasound imaging system) is provided. The system includes a portable host system having one or more processors and a memory for storing a plurality of applications that include corresponding programmed instructions. The one or more processors configured to execute programmed instructions of a select application when the select application is activated by performing one or more operations. The one or more operations may include obtain a set of frames of 2D ultrasound images, develop a prospect model indicating a likelihood that frames within the set include an organ of interest (OOI), identify primary and secondary reference frames from the set of the frames based on the prospect model, determine a characteristic of interest in the primary reference frame, select a candidate shape for the OOI based on the character of interest in the primary reference frame, and adjust the candidate shape based on the secondary reference frames to form a resultant shape for the OOI.

In an embodiment a tangible and non-transitory computer readable medium including one or more programmed instructions configured to direct one or more processors is provided. The one or more processors are directed to obtain a set of frames of 2D ultrasound images, develop a prospect model indicating a likelihood that frames within the set include an organ of interest (OOI), identify primary and secondary reference frames from the set of the frames based on the prospect model, determine a characteristic of interest in the primary reference frame, select a candidate shape for the OOI based on the character of interest in the primary reference frame, and adjust the candidate shape based on the secondary reference frames to form a resultant shape for the OOI.

DETAILED DESCRIPTION OF THE INVENTION

Figure 1:
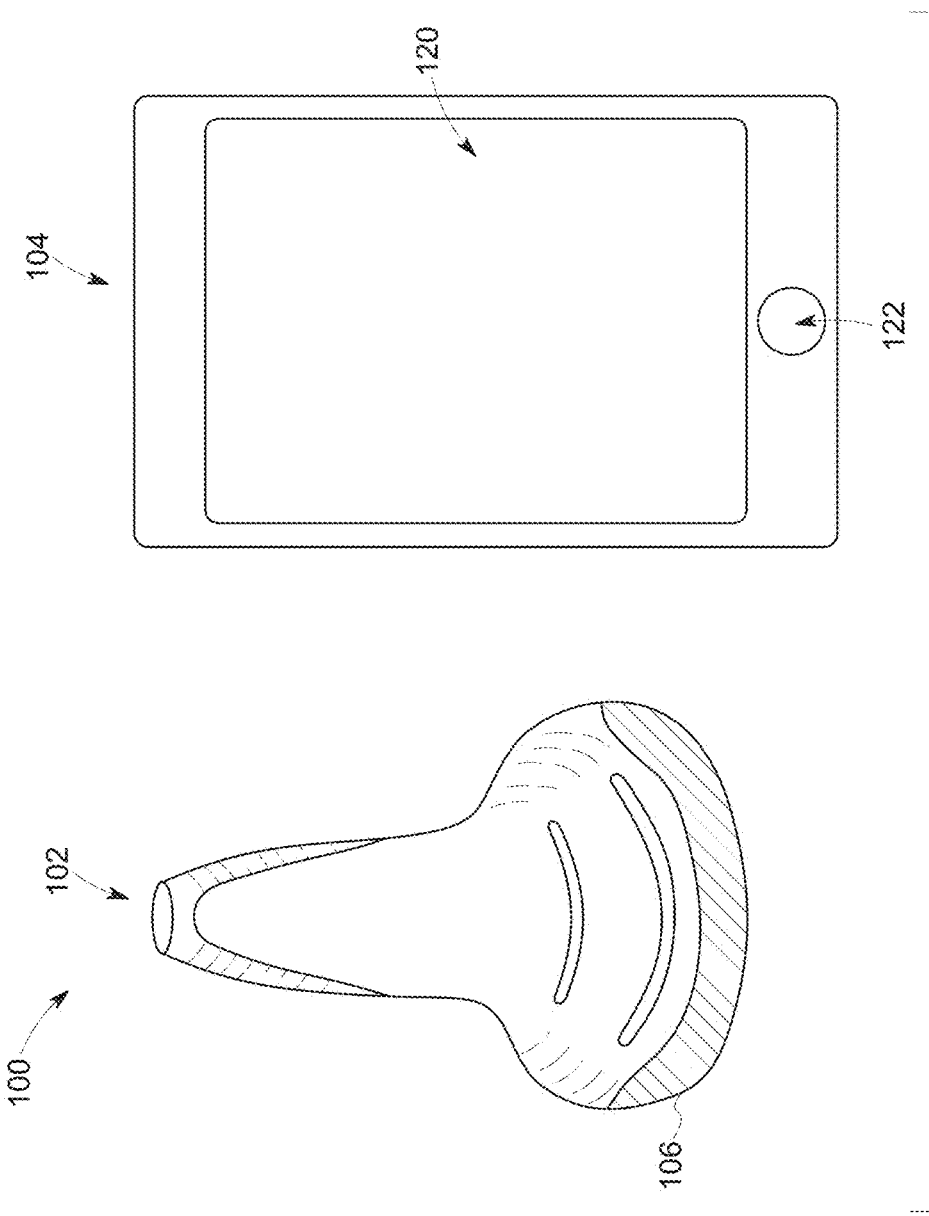
FIG. 1 illustrates an exemplary mobile ultrasound imaging system formed, in accordance with various embodiments described herein.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Described herein are various embodiments for a mobile ultrasound imaging system utilizing an automatic volume technique for faster and accurate volume measurements of an organ of interest, such as a bladder. The mobile ultrasound imaging system may include a portable host system that executes an automatic method for calculating a volume from a set of frames of two dimensional (2D) ultrasound images of an organ of interest. For example, the frames may correspond to B-mode ultrasound images. The frames of 2D ultrasound images are based on ultrasound data acquired by an ultrasound probe when a patient is scanned in a lateral fashion. The ultrasound probe includes an inertial measurement circuit, which is configured to acquire sensor measurement values of the ultrasound probe during the scan. The sensor measurement values are utilized by the controller circuit of the portable host system to determine a position and/or tilt angle of the ultrasound probe 102 during acquisition of the frames. For example, sensor measurement values of the inertial measurement circuit may be generated by a plurality of sensor of the inertial measurement circuit, such as an accelerometer, a gyroscope, and/or the like. Each of the positional measurements and the frames generated by the controller circuit include corresponding time stamp values, which are stored in a memory of the mobile ultrasound imaging system. A controller circuit of the mobile ultrasound imaging system is configured to identify the organ of interest within the frames based on a segmentation algorithm. Utilizing the identified frames having the organ of interest and the positional measurements, the controller circuit may generate a 3D representation of the organ of interest. Based on the 3D representation, the controller circuit is configured to calculate a volume of the organ of interest.

A technical effect of at least one embodiment includes an automated solution to easily acquire ultrasound data and measure an organ of interest, which allows the mobile ultrasound imaging system to be used by nonconventional ultrasound users. A technical effect of at least one embodiment includes increased accuracy of dimensional measurements of the organ of interest.

Various embodiments described herein may be implemented as a mobile ultrasound imaging system 100 as shown in FIG. 1. More specifically, FIG. 1 illustrates an exemplary mobile ultrasound imaging system 100 that is constructed in accordance with various embodiments. The ultrasound imaging system 100 includes a portable host system 104 and an ultrasound probe 102. The portable host system 104 may be a portable hand-held device, for example, a mobile phone such as a smart phone, a tablet computer, and/or the like. The portable host system 104 may support one or more applications that are executed by a controller circuit 202, shown in FIG. 2, of the portable host system 104.

An application may correspond to one or more software modules stored in a memory 204 that when executed by the controller circuit 202, the controller circuit 202 is configured to perform one or more coordinated functions, tasks, and/or activities. One or more applications may correspond to medical imaging functions such as an ultrasound imaging application, medical diagnostic tools (e.g., organ volume), and/or the like. Additionally or alternatively, one or more applications may correspond to non-medical imaging functions (e.g., not using or based on acquiring ultrasound data) such as a word processing application, a disc authoring application, a gaming application, a telephone application, an e-mail application, an instant messaging application, a photo management application, a digital camera application, a web browsing application, a GPS mapping application, a digital music player application, a digital video player application, and/or the like. Optionally, one or more of the applications may be received by the portable host system 104 remotely. The one or more applications may be executed on the portable host system 104, and use a common physical user interface, such as a touchscreen display 120 (e.g., a touch-sensitive display) or one or more tactile buttons 122.

For example, the touchscreen display 120 may display information corresponding to one or more user selectable icons 302-316 (shown in FIG. 3) of a graphical user interface (GUI). One or more functions of the touchscreen display 120 as well as the corresponding information displayed on the device may be adjusted and/or varied from one application to the next and/or within a respective application.

The ultrasound probe 102 includes a transducer array 106, such as a phased array having electronics to perform sub-aperture (SAP) beamforming. For example, transducer array 106 may include piezoelectric crystals that emit pulsed ultrasonic signals into a body (e.g., patient) or volume. The ultrasonic signals may include, for example, one of more reference pulses, one or more pushing pulses (e.g., sheer-waves), and/or one or more tracking pulses. At least a portion of the pulsed ultrasonic signals are back-scattered from structures in and around the OOI and measured by the ultrasound probe 102. The ultrasound probe 102 may be connected wirelessly or with a cable to the host system 104. In one embodiment, the ultrasound probe 104 may be a universal probe which integrates both a phased array transducer and a linear transducer into the same probe housing.

Figure 2:
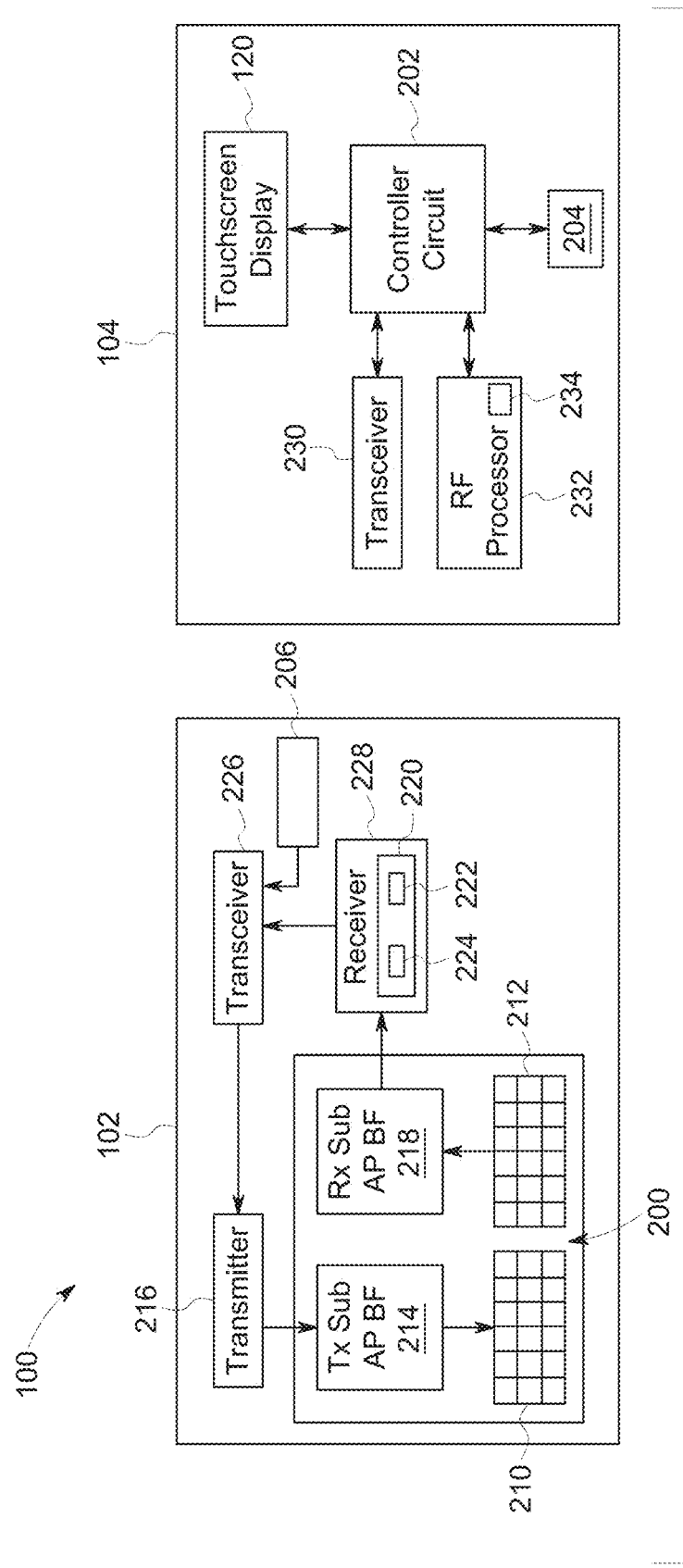
FIG. 2 is a system block diagram of the mobile ultrasound imaging system shown in FIG. 1.

In various embodiments, the ultrasound probe 102 may include an analog front end (AFE) 220, shown in FIG. 2, which may include built-in electronics that enable the ultrasound probe 102 to transmit digital signals to the portable host system 104. The portable host system 104 then utilizes the digital signals to reconstruct an ultrasound image based on the information received from the ultrasound probe 102.

FIG. 2 is a schematic block diagram of the imaging system 100 shown in FIG. 1. In various embodiments, the ultrasound probe 102 includes a two-dimensional (2D) array 200 of elements. The ultrasound probe 102 may also be embodied as a 1.25 D array, a 1.5 D array, a 1.75 D array, a 2D array, and/or the like. Optionally, the ultrasound probe 102 may be a stand-alone continuous wave (CW) probe with a single transmit element and a single receive element. In various embodiments, the 2D array 200 may include a transmit group of elements 210 and a receive group of elements 212. A sub-aperture transmit beamformer 214 controls a transmitter 216, which through transmit sub-aperture beamformers 214, drives the group of transmit elements 210 to emit, for example, CW ultrasonic transmit signals into a region of interest (e.g., human, animal, cavity, physical and/or anatomical structure, and/or the like) that includes an organ of interest (OOI) (e.g., bladder, kidney, stomach, heart, uterus, liver, and/or the like). The transmitted CW ultrasonic signals are back-scattered from structures in and around the OOI, like blood cells, to produce echoes which return to the receive group of elements 212. The receive group of elements 212 convert the received echoes into analog signals as described in more detail below. A sub-aperture receive beamformer 218 partially beamforms the signals received from the receive group of elements 212 and then passes the partially beamformed signals to a receiver 228.

The sub-aperture transmit beamformer 214 may be configured to reduce a number of system channels utilized to process signals from the large number of transducer elements 210. For example, assume that there are m elements 210. In various embodiments, m channels are then utilized to couple the m elements 210 to the sub-aperture beamformer 214. The sub-aperture beamformer 214 then functions such that n channels of information are passed between the transmitter 216 and the sub-aperture beamformer 214, wherein n <m. Moreover, assume that there are m elements 212. In various embodiments, m channels are then utilized to couple the m elements 212 to the sub-aperture beamformer 218. The sub-aperture beamformer 218 then functions such that n channels of information are passed between the receiver 228 and the sub-aperture beamformer 218, wherein n<m. Thus, the sub-aperture beamformers 214 and 218 function to output fewer channels of information than are received from the elements 210 and 104.

In various embodiments, the receiver 228 may include the AFE 220. The AFE 220 may include for example, a plurality of demodulators 224 and a plurality of analog/digital (A/D) converters 222. In operation, the complex demodulators 224 demodulate the RF signal to form IQ data pairs representative of the echo signals. The I and Q values of the beams represent in-phase and quadrature components of a magnitude of echo signals. More specifically, the complex demodulators 224 perform digital demodulation, and optionally filtering as described in more detail herein. The demodulated (or down-sampled) ultrasound data may then be converted to digital data using the A/D converters 222. The A/D converters 222 convert the analog outputs from the complex demodulators 224 to digital signals that are then transmitted to the portable host system 104 via a transceiver 226.

The transceiver 226 may include hardware, such as a processor, controller circuit, or other logic based devices to transmit, detect and/or decode wireless data received by an antenna (not shown) of the transceiver 226 based on a wireless protocol to and/or from the portable host system 104. For example, the wireless protocol may be Bluetooth, Bluetooth low energy, ZigBee, and/or the like. Additionally or alternatively, the ultrasound probe 102 may be physically coupled to the portable host system 104 via a cable. For example, the digital information may be received by the portable host system 104 from the ultrasound probe 102 along the cable.

The beamformers 214 and 218, and the complex demodulators 224 facilitate reducing the quantity of information that is transmitted from the ultrasound probe 102 to the portable host system 104. Accordingly, the quantity of information being processed by the portable host system 104 is reduced and ultrasound images of the patient may be generated, by the portable host system 104, in real-time as the information is being acquired from the ultrasound probe 102.

The ultrasound probe 102 includes an inertial measurement circuit 206. The inertial measurement circuit 206 is configured to acquire sensor measurement values of the ultrasound probe 102 that are then transmitted to the portable host system 104 via the transceiver 226. The sensor measurement values are utilized by the controller circuit 202 to determine a tilt angle of the ultrasound probe 102, a position of the ultrasound probe 102, and/or the like. The sensor measurement values are generated by a plurality of sensors of the inertial measurement circuit 206, such as an accelerometer, a gyroscope, and/or the like. For example, the accelerometer may generate sensor measurement values representing proper accelerations along three orthogonal axes. In another example, the gyroscope may generate sensor measurement values representing a rotational and/or angular velocity of the ultrasound probe 102.

The portable host system 104 may include a controller circuit 202 operably coupled to the memory 204, the touch-screen display 120, and the transceiver 230. The controller circuit 202 may include one or more processors. Additionally or alternatively, the controller circuit 202 may include a central controller circuit (CPU), one or more microprocessors, a graphics controller circuit (GPU), or any other electronic component capable of processing inputted data according to specific logical instructions. The controller circuit 202 may execute programmed instructions stored on a tangible and non-transitory computer readable medium (e.g., memory 204, integrated memory of the controller circuit 202 such as EEPROM, ROM, or RAM) corresponding to one or more applications. For example, when a select application is activated by the user, the controller circuit 202 executes the programmed instructions of the select application.

The transceiver 230 may include hardware, such as a processor, controller, or other logic based device to transmit, detect and/or decode wireless data received by an antenna (not shown) of the transceiver 230 based on a wireless protocol (e.g., Bluetooth, Bluetooth low energy, ZigBee, and/or the like). For example, the transceiver 230 may transmit to and/or receive wireless data that includes ultrasound data from the transceiver 226 of the ultrasound probe 102 and/or sensor measurement values generated by the inertial measurement circuit 206.

In various embodiments, the host system 104 may include hardware components, including the controller circuit 202, that are integrated to form a single "System-On-Chip" (SOC). The SOC device may include multiple CPU cores and at least one GPU core. The SOC may be an integrated circuit (IC) such that all components of the SOC are on a single chip substrate (e.g., a single silicon die, a chip). For example, the SOC may have the memory 204, the controller circuit 202, the transceiver 230 embedded on a single die contained within a single chip package (e.g., QFN, TQFP, SOIC, BGA, and/or the like).

The touchscreen display 120 may include a liquid crystal display, an organic light emitting diode display, and/or the like overlaid with a sensor substrate (not shown). The sensor substrate may include a transparent and/or optically transparent conducting surface, such as indium tin oxide (ITO), a metal mesh (e.g., a silver nano-tube mesh, and carbon match, a graph feed mesh), and/or the like. The sensor substrate may be configured as an array of electrically distinct rows and columns of electrodes that extend through a surface area of the touchscreen display 120. The sensor substrate may be coupled to a touchscreen controller circuit (not shown).

A touchscreen controller circuit may include hardware, such as a processor, a controller, or other logic-based devices and/or a combination of hardware and software which is used to determine a position on the touchscreen display 120 activated and/or contacted by the user (e.g., finger(s) in contact with the touchscreen display 120). In various embodiments, the touchscreen controller circuit may be a part of and/or integrated with the controller circuit 202 and/or apart of the touchscreen display 120. The touchscreen controller circuit may determine a user select position activated and/or contacted by the user by measuring a capacitance for each electrode (e.g., self-capacitance) of the sensor substrate.

For example, the touchscreen controller circuit may transmit a current drive signal along a single electrode and measure a capacitance along the single electrode. Additionally or alternatively, the touchscreen controller circuit may measure a capacitance for each intersection of a row and column electrode (e.g., mutual capacitance). For example, the touchscreen controller circuit may transmit a current drive signal along a first electrode (e.g., a row electrode, a column electrode) and measure a mutual capacitance from a second electrode (e.g., a column electrode, a row electrode). Based on the measured capacitance, the touchscreen controller circuit may determine whether a finger(s) from the user is in contact and/or proximate to the sensor substrate. For example, when the capacitance, of the single electrode or intersection, is above a predetermined threshold the touchscreen controller circuit may determine that the user is activating the corresponding single electrode or intersection. Further, based on a location of the corresponding single electrode or intersection, the touchscreen controller circuit may determine a position of the finger with respect to the touchscreen display 120. In another example, when the capacitance is below a predetermine threshold the touchscreen controller circuit may determine that the single electrode or intersection is not activated. The touchscreen controller may output the user select position of the user input to the controller circuit 202. In connection with FIG. 3, the controller circuit 202 may determine activation of a select application based on the user select position of the contact by the user.

Figure 3:
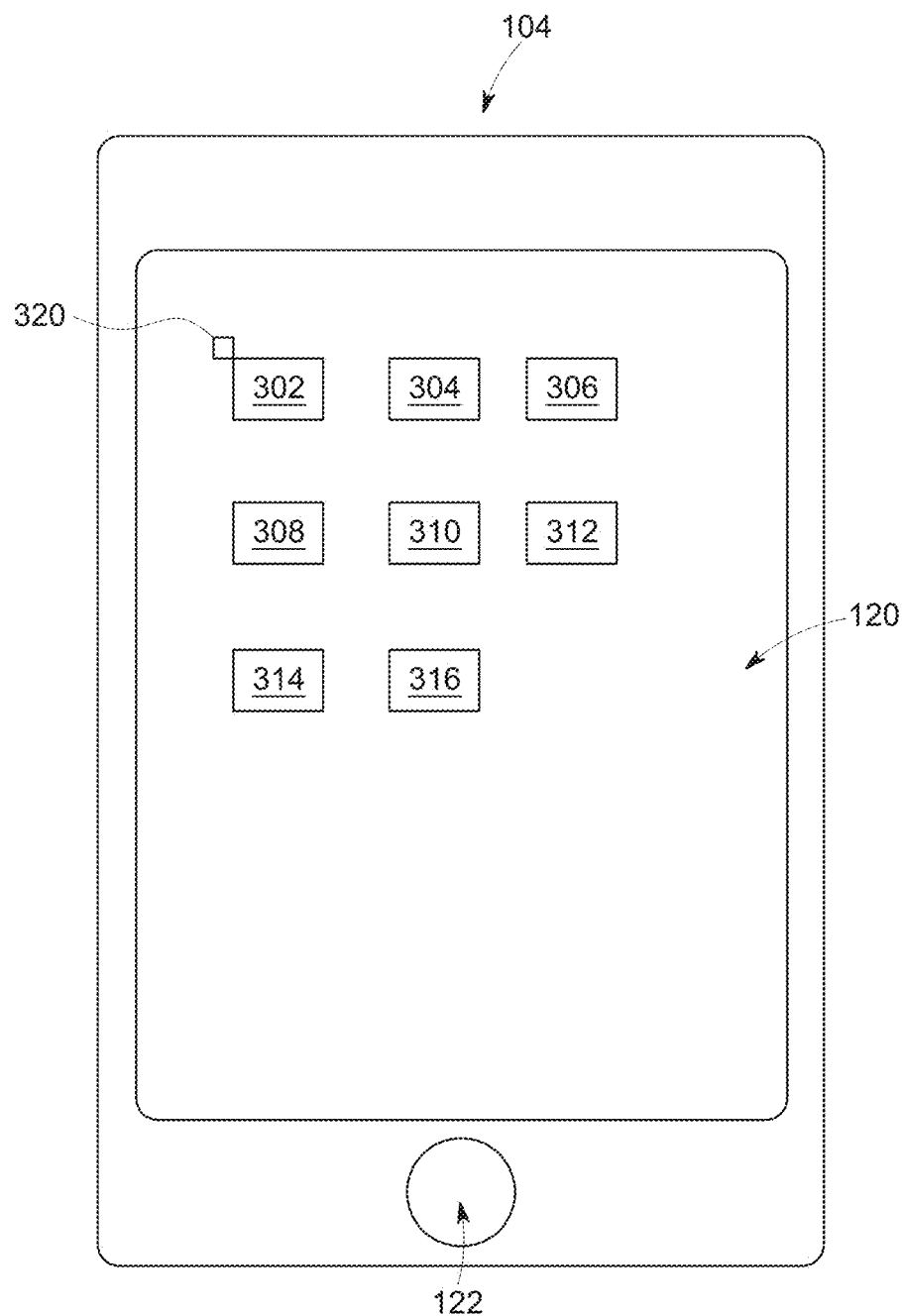
FIG. 3 is a screen shot of a graphical user interface shown on a touchscreen display of a host system shown in FIG. 1, in accordance with various embodiments described herein.

FIG. 3 is a screen shot of a GUI shown on the touchscreen display 120. The GUI may include one or more interface components, such as one or more user selectable icons 302-316 illustrated in FIG. 3. The interface components correspond to user selectable elements shown visually on the touchscreen display 120, and may be selected, manipulated, and/or activated by the user operating the touchscreen display 120. The interface components may be presented in varying shapes and colors. Optionally, the interface components may include text or symbols.

It should be noted that the layout of the icons 302-316 is merely for illustration and different layouts may be provided. Each of the one or more user selectable icons 302-316 may correspond to an application stored in the memory 204 and executable by the controller circuit 202. In various embodiments, the icons 302-316 may include, for example, an ultrasound imaging application 302, a web browser application 304, an e-mail application 306, a GPS mapping application 306, a telephone application 308, a word processing application 310, a digital music player application 312, a digital video application 314, a digital camera application 316, and various other icons. The user selectable icons 302-316 may be any graphical and/or text based selectable element. For example, the icon 302 may be shown as an image of an ultrasound probe.

The controller circuit 202 may determine when one of the selectable icons 302-316 and corresponding application is selected by the user select position determined from the touchscreen controller is approximately the same and/or within a predetermined distance of a position of a corresponding icon 302-316. For example, the controller circuit 202 may receive a user select position 320 from the touchscreen controller. Since the user select position 320 is adjacent to or overlaid with the ultrasound imaging application 302, the controller circuit 202 may determine that the ultrasound imaging application 302 is selected by the user. When selected, the controller circuit 202 may execute the programmed instructions corresponding to the selected icon 302-316. For example, FIG. 4, when the ultrasound imaging application 302 is selected, the controller circuit 202 may execute programmed instructions corresponding to the ultrasound imaging application.

Figure 4A:
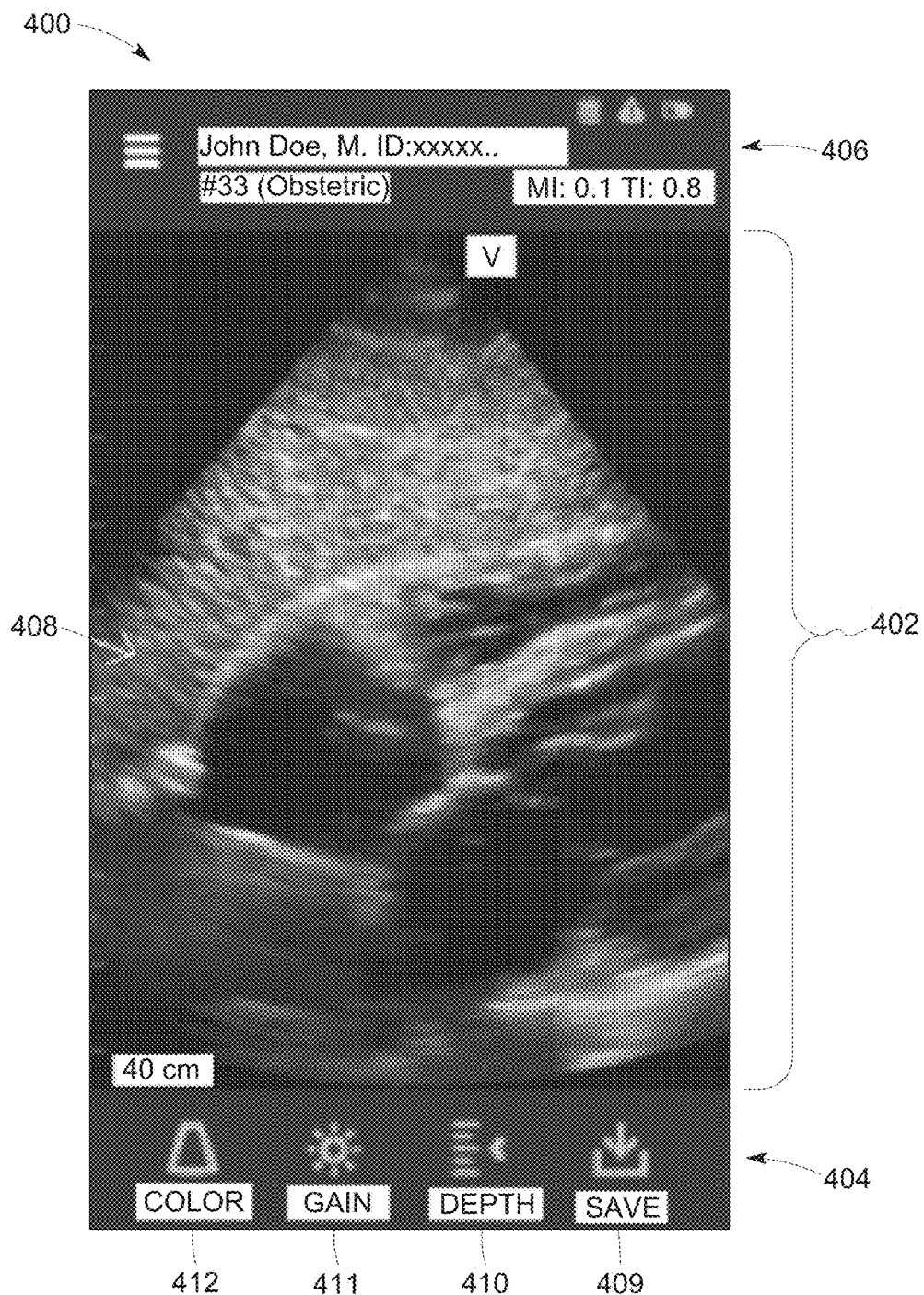
FIG. 4A is a screen shot of a graphical user interface on the touchscreen display of a host system shown in FIG. 1, in accordance with various embodiments described herein.

FIG. 4A illustrates a GUI 400 displayed on the touchscreen display 120 of the host system 104 when the ultrasound imaging application is selected based on the programmed instructions corresponding to the ultrasound imaging application. The GUI 400 may include one or more interface components (e.g., menu bar 404, title bar 406) and an activity window 402.

The activity window 402 may correspond to an area of the GUI 400 for viewing results or outcomes of one or more operations performed by the controller circuit 202. For example, the activity window 402 may include one or more ultrasound images 408, ultrasound videos, measurements, diagnostic results, data entry (e.g., patient information), and/or the like. It should be noted in various other embodiments the activity window 402 may be larger or smaller relative to the one or more interface components as illustrated in FIG. 4. Optionally the activity window 402 may be in a full-screen mode. For example, a size of the activity window 402 may encompass the touchscreen display 120.

The title bar 406 may identify information of the patient, user information, data and/or time information, and/or the like during operation of the ultrasound imaging application.

The menu bar 404 may correspond to a list of textual or graphical user selectable elements from which the user may select. For example, the menu bar 404 may include one or more icons 409-412 that correspond to one or more operations or functions that may be performed by the controller circuit 202 when selected by the user.

For example, when the controller circuit 202 executes programmed instructions corresponding to the ultrasound imaging application, the controller circuit 202 may start acquiring ultrasound data from the ultrasound probe 102. In connection with FIG. 4B, during acquisition, the ultrasound probe 102 may be tilted along a lateral axis 418 by the user to obtain a set of frames 416 of 2D ultrasound images.

Figure 4B:
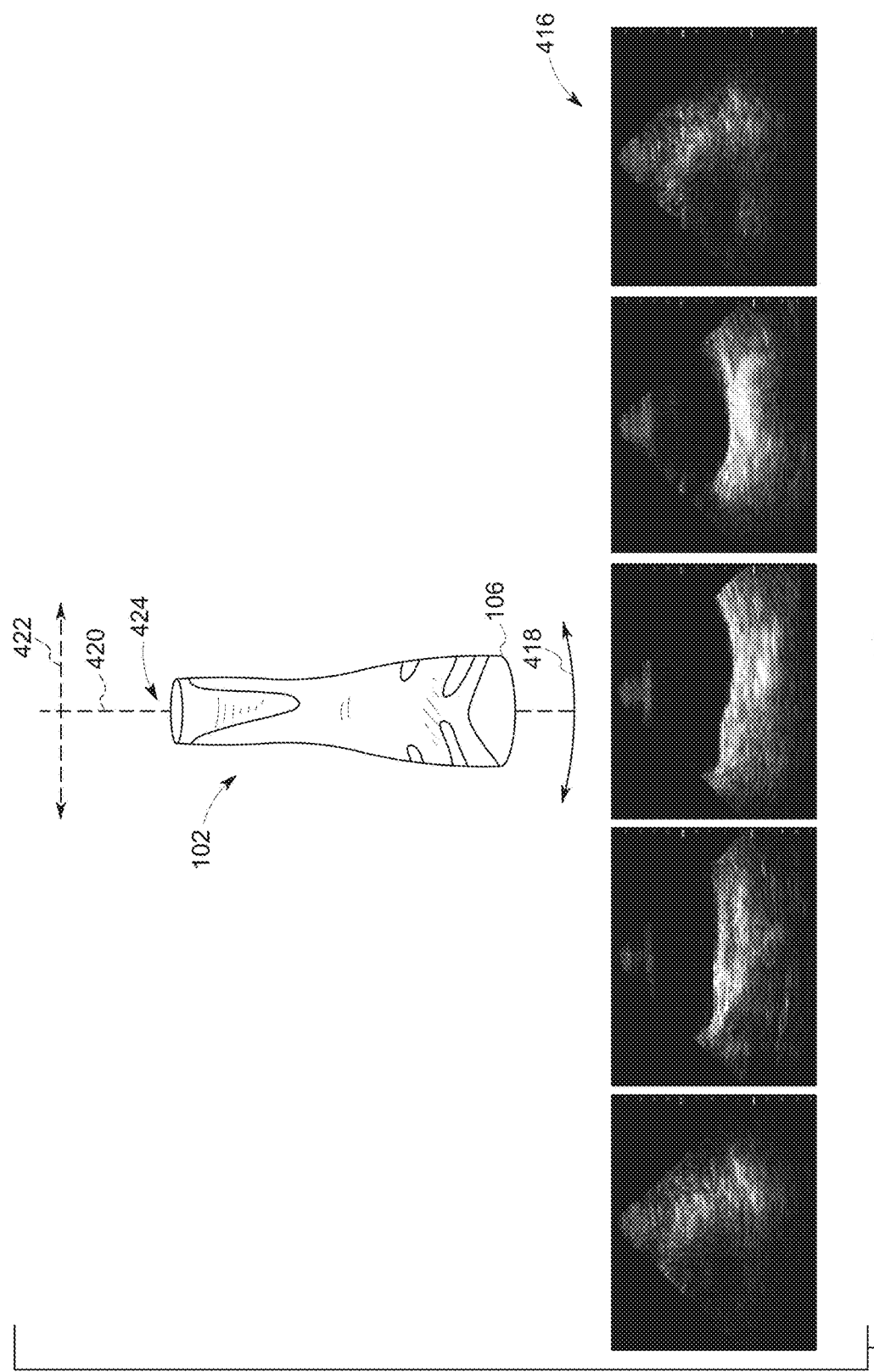
FIG. 4B is an illustration of a set of frames of 2D ultrasound images obtained by an ultrasound probe along a lateral axis, in accordance with various embodiments described herein.

FIG. 4B is an illustration of the set of frames 416 of 2D ultrasound images obtained by the ultrasound probe 102 along the lateral axis 418, in accordance with various embodiments described herein. It may be noted that the ultrasound probe 102 shown in FIG. 4B is a different view than the ultrasound probe 102 shown in FIG. 1. The ultrasound probe 102 shown in FIG. 4B is a side view relative to the ultrasound probe 102 of FIG. 1. For example, the ultrasound probe 102 of FIG. 1 is positioned normal to an axis 422 shown in FIG. 4B.

The ultrasound probe 102 may be tilted by repositioning a distal end 424 of the ultrasound probe 102 to align a z-axis 420 of the ultrasound probe 102 at different positions along the lateral axis 418 to form tilt angles to acquire the set of frames 416. For example, the user may adjust an angle of the ultrasound probe 102 relative to the patient, region of interest, and/or OOI. The different angles of the ultrasound probe 102 aligns the ultrasound signals emitted from the transducer array 106 at different positions along the lateral axis 418. Based on the ultrasound data received at the different angles, the controller circuit 202 generates a set of frames 416 of 2D ultrasound images. Each of the 2D ultrasound images correspond to ultrasound data acquired at different points along the lateral axis 418. Optionally, the user may select one of the icons 410-412 to begin and/or adjust acquisition settings for the acquisition of the frames 416 of the 2D ultrasound images (e.g., adjust a gain, B-mode acquisition, color flow, gain, and/or the like), select the icon 409 to save ultrasound images displayed in the activity window 402 to be used for diagnostic or measurement tools (e.g., measuring a volume of the OOI) by the controller circuit 202, and/or the like. It may be noted that in various embodiments, a number of frames within the set of frames 416 may be more and/or less than what is shown in FIG. 4B.

The programmed instructions for the one or more icons 409-412 (e.g., to acquire ultrasound images) may be included within the programmed instructions of the ultrasound imaging application stored in the memory 204 (FIG. 2), which includes algorithms for beamforming as well as subsequent signal and image processing steps utilized to process (e.g., an RF processor 232) and display the ultrasound information received from the ultrasound probe 102. In operation, the algorithms stored in the memory 204 may be dynamically configured or adjusted by the controller circuit 202 according to a probe/application as well as the computing and/or power supply capabilities of the host system 104. The controller circuit 202 may execute the beamforming algorithm stored in the memory 204 to perform additional or final beamforming to the digital ultrasound information received from the ultrasound probe 102, and outputs a radio frequency (RF) signal. Additionally or alternatively, the portable host system 104 may include a receive beamformer (not shown), which receives the digital ultrasound information and performs the additional or final beamforming. The RF signal is then provided to an RF processor 232 that processes the RF signal. The RF processor 232 may include a complex demodulator 232 that demodulates the RF signal to form IQ data pairs representative of the echo signals, and one or more processors. The RF or IQ signal data may then be provided directly to the memory 204 for storage (e.g., temporary storage). Optionally, the output of the RF processors 232 may be passed directly to the controller circuit 202. Additionally or alternatively, the RF processor 232 may be integrated with the controller circuit 202 corresponding to programmed instructions of the ultrasound imaging application stored in the memory 204.

The controller circuit 202 may further process the output of the RF processor 232 and to generate the frames 416 of the 2D ultrasound images for display on the touchscreen display 120. In operation, the controller circuit 202 is configured to perform one or more processing operations according to a plurality of selectable ultrasound modalities on the acquired ultrasound data.

Figure 5:
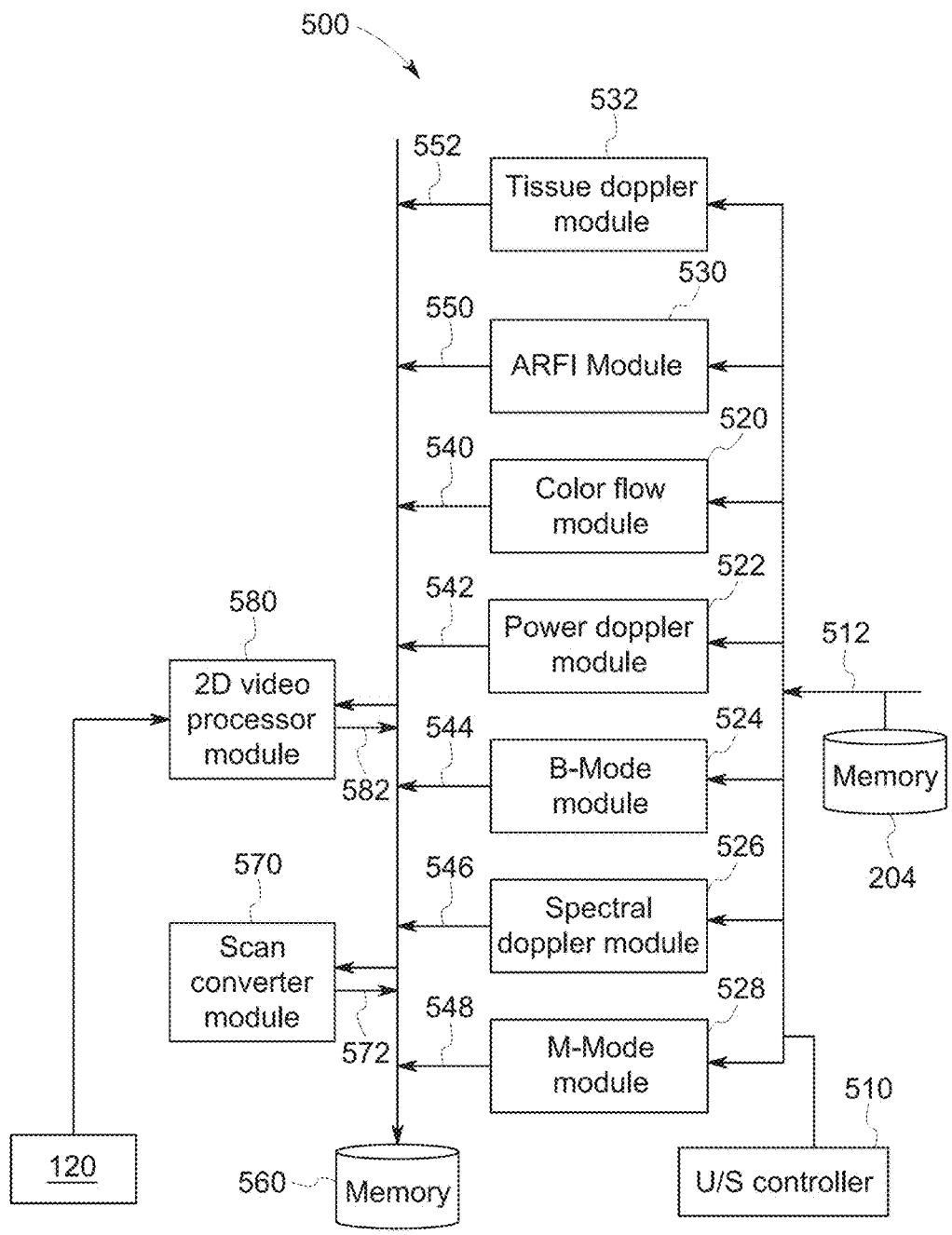
FIG. 5 is a block diagram of an ultrasound processor module of a host system shown in FIG. 1, in accordance with various embodiments described herein.

FIG. 5 illustrates an exemplary block diagram of an ultrasound processor module 500, which may be embodied in the controller circuit 202 of FIG. 2 or a portion thereof. The ultrasound processor module 500 is illustrated conceptually as a collection of sub-modules corresponding to operations that may be performed by the controller circuit 202 when executing programmed instructions for acquiring ultrasound images. Optionally, the one or more sub-modules may be implemented utilizing any combination of dedicated hardware boards, DSPs, processors, and/or the like of the host system 104. Additionally or alternatively, the sub-modules of FIG. 5 may be implemented utilizing one or more processors, with the functional operations distributed between the processors, for example also including a Graphics Processor Unit (GPU). As a further option, the sub-modules of FIG. 5 may be implemented utilizing a hybrid configuration in which certain modular functions are performed utilizing dedicated hardware, while the remaining modular functions are performed utilizing a processor. The sub-modules also may be implemented as software modules within a processing unit.

The operations of the sub-modules illustrated in FIG. 5 may be controlled by a local ultrasound controller 510 or by the controller circuit 202. The controller circuit 202 may receive ultrasound data 512 in one of several forms. In the exemplary embodiment of FIG. 2, the received ultrasound data 512 constitutes IQ data pairs representing the real and imaginary components associated with each data sample. The IQ data pairs are provided to one or more of a color-flow sub-module 520, a power Doppler sub-module 522, a B-mode sub-module 524, a spectral Doppler sub-module 526 and an M-mode sub-module 528. Optionally, other sub-modules may be included such as an Acoustic Radiation Force Impulse (ARFI) sub-module 530 and a Tissue Doppler (TDE) sub-module 532, among others.

Each of sub-modules 520-532 are configured to process the IQ data pairs in a corresponding manner to generate color-flow data 540, power Doppler data 542, B-mode data 544, spectral Doppler data 546, M-mode data 548, ARFI data 550, and tissue Doppler data 552, all of which may be stored in a memory 560 (or memory 204 shown in FIG. 2) temporarily before subsequent processing. For example, the B-mode sub-module 524 may generate B-mode data 544 including a plurality of B-mode ultrasound images corresponding to the frames 416.

The data 540-552 may be stored in the memory 560, for example, as sets of vector data values, where each set defines an individual ultrasound image frame. The vector data values are generally organized based on the polar coordinate system. Alternately or additionally the data may be stored as beamformed IQ data in the memory 204.

A scan converter sub-module 570 accesses and obtains from the memory 560 the vector data values associated with an image frame and converts the set of vector data values to Cartesian coordinates to generate an ultrasound image frames 572 (e.g., one of the frames 416) formatted for display on the display 120. The ultrasound image frames 572 generated by the scan converter module 570 may be provided back to the memory 560 for subsequent processing or may be provided to the memory 204.

Once the scan converter sub-module 570 generates the ultrasound image frames 572 associated with, for example, the B-mode ultrasound image data, and/or the like, the image frames 572 may be restored in the memory 560 or communicated over a bus 574 to a database (not shown), the memory 560, the memory 204, and/or to other processors.

The scan converted data may be converted into an X, Y format for display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the touchscreen display 120 (shown in FIG. 2) to display the image frame within the activity window 402. The image displayed within the activity window 402 may be produced from image frames of data in which each datum indicates the intensity or brightness of a respective pixel in the display.

Referring again to FIG. 5, a video processor sub-module 580 may combine one or more of the frames generated from the different types of ultrasound information. For example, the video processor sub-module 580 may combine different image frames by mapping one type of data to a grey map and mapping the other type of data to a color map for video display. In the final displayed 2D ultrasound image, color pixel data may be superimposed on the grey scale pixel data to form a single multi-mode image frame 582 (e.g., functional image) that is again re-stored in the memory 560 or communicated over the bus 574. Successive frames of 2D ultrasound images may be stored as a cine loop in the memory 260 or the memory 204. The cine loop represents a first in, first out circular image buffer to capture image data that is displayed to the user. The user may freeze the cine loop by entering and/or selecting a freeze command using an interface component shown on the GUI 400 of the touchscreen display 120.

Returning to FIG. 4, the ultrasound imaging application includes diagnostic tools, which may be used by the user on the frames 416 of the 2D ultrasound images 408 acquired by the portable host system 104, as described above, or stored in the memory 204 (e.g., acquired remotely, acquired previously). For example, the user may select an organ volume application within the ultrasound imaging application by selecting a diagnostic and measurement icon (e.g., one of the icons 409-412). Based on the selection of the diagnostic and measurement icon, the controller circuit 202 may be configured to perform, execute, and/or the like programmed instructions stored in the memory 204 corresponding to a workflow (e.g., operations of the method 600) corresponding to the organ volume application.

Figure 6:
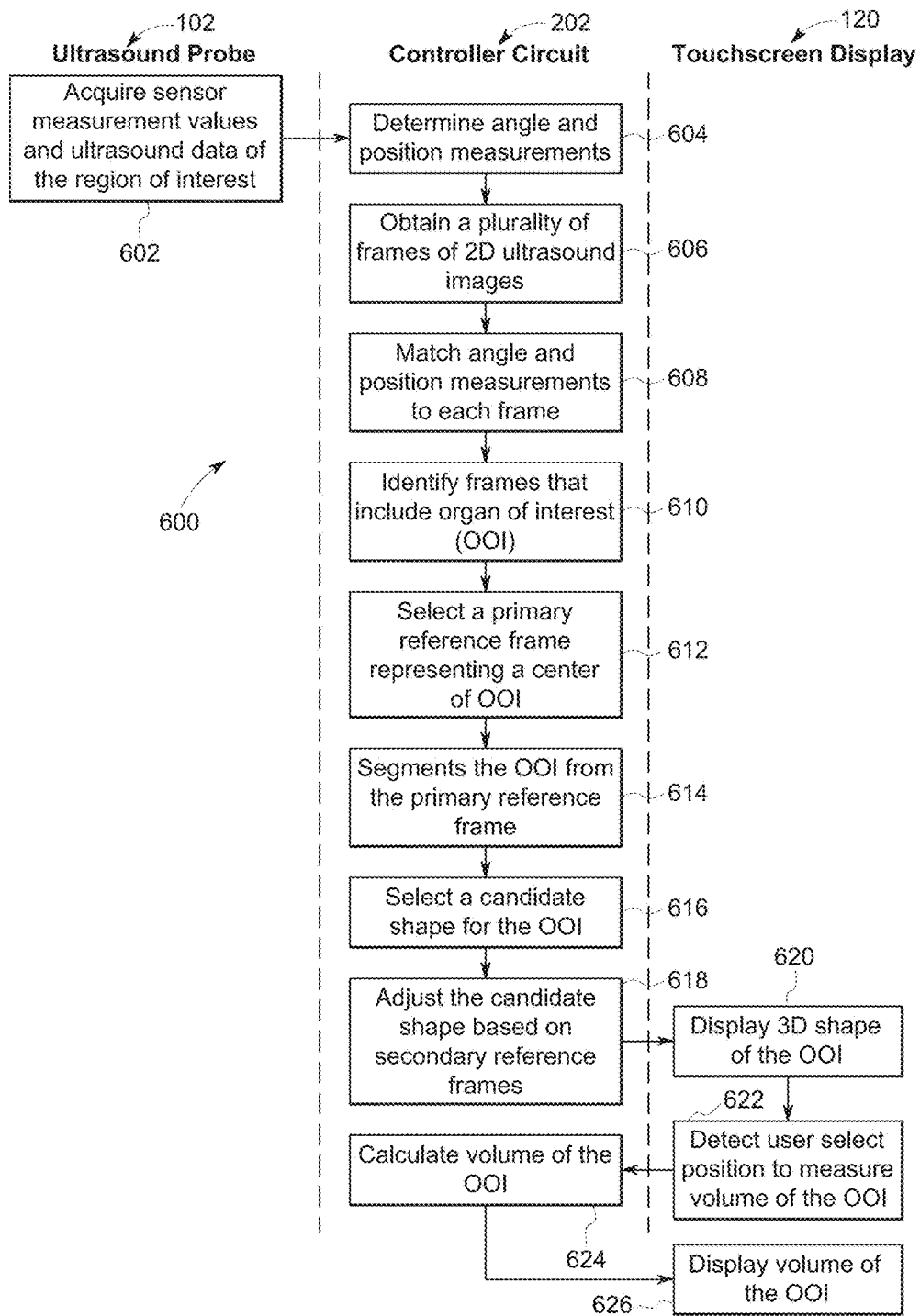
FIG. 6 illustrates a swim lane diagram illustrating a method of using a mobile ultrasound imaging system to determine a volume of an organ of interest, in accordance with various embodiments described herein.

FIG. 6 illustrates a swim lane diagram of the method 600 for using a mobile ultrasound system 100 to determine a volume of an organ of interest (OOI) from the set of frames 416 of 2D ultrasound images. The method 600, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be used as one or more algorithms or applications to direct hardware to perform one or more operations described herein. It should be noted, other methods may be used, in accordance with embodiments herein.

Beginning at 602, the ultrasound probe 102 obtains sensor measurement values of the ultrasound probe 102 and ultrasound data of the region of interest (ROI). During a scan of the ROI, which includes the organ of interest, the ultrasound probe 120 may be continually adjusted along the lateral axis 418 (FIG. 4) by the user. For example, the user may adjust a tilt angle of the transducer array 106 (FIG. 1) in relative to the patient, region of interest, and/or OOI. The different angles of the ultrasound probe 102 aligns the ultrasound signals emitted from the transducer array 106 at different positions along the lateral axis 418. At each of the angles, the transducer array 106 (such as the receive group of elements 212) may receive echoes corresponding to structures of the ROI. The receive echoes are partially beamformed and received by the portable host system 104 as ultrasound data.

As the ultrasound probe 102 is adjusted along the lateral axis 418, the inertial measurement circuit 206 (FIG. 2) is configured to generate sensor measurement values of the ultrasound probe 102, which is utilized by the controller circuit 202 generate positon measurements of the ultrasound probe 102. For example, the accelerometer and a gyroscope of the inertial measurement circuit 206 generates sensor measurement values over time during the scan. The sensor measurement values may represent proper accelerations of the ultrasound probe 102 along a three orthogonal axes, a rotational and/or angular velocity of the ultrasound probe 102, and/or the like. The sensor measurements values received by the portable host system 104. For example, the sensor measurement values are transmitted with and/or concurrently with the ultrasound data by the transceiver 226, and are received by the transceiver 230.

At 604, the controller circuit 202 determines angle and position measurements of the ultrasound probe 102. The sensor measurement values are utilized by the controller circuit 202 to determine angle (e.g., tile angle) and the position measurements of the ultrasound probe over time during the scan. Optionally, the position measurements may be based on a noise correction algorithm executing by the controller circuit 202. For example, over time the sensor measurement values of the accelerometer, the gyroscope, and/or the like may drift over time. The noise correction algorithm may utilize sensor measurement values generated by the plurality of sensors of the inertial measurement circuit 206 to reduce the effect of the drift of the sensors to the sensor measurement values.

For example, the controller circuit 202 calculate the position measurements of the ultrasound probe 102 based on the sensor measurement values acquired by the inertial measurement circuit 206. The controller circuit 202 may rotate the sensor measurement values generated by the accelerometer to a global axis using the using the sensor measurement values from the gyroscope. For example, the controller circuit 202 combines the rotated sensor measurement values of the accelerometer and the sensor measurement values of the gyroscope to project the sensor measurement values to the global axis. The controller circuit 202 may correct the combined sensor measurement values with a theoretical position of the ultrasound probe 102 using a linear quadratic estimation (e.g., Kalman filtering), dead reckoning algorithm, and/or the like. The theoretical position of the ultrasound probe 102 may be based on priori information stored in the memory 204. The priori information may be a trend of sensor measurement values based on a plurality of prior scans, such as from clinical trials. For example, the controller circuit 202 may execute a principal component analysis on the priori information to generate the trend of sensor measurement values. Additionally or alternatively, the controller circuit 202 may be configured to adjust the trend utilizing a singular value decomposition algorithm.

In another example, the controller circuit 202 calculates the angle (e.g., tilted angle) of the ultrasound probe 102 based on the sensor measurement values acquired by the inertial measurement circuit 206. The controller circuit 202 is configured to utilize a linear quadratic estimation (e.g., Kalman filtering) to combine the sensor measurement values of the accelerometer and the gyroscope to calculate the angle of the ultrasound probe 102.

At 606, the controller circuit 202 generates a set of frames of 2D ultrasound images based on the ultrasound data acquired by the ultrasound probe 102. Based on the ultrasound data received at the different angles, the controller circuit 202 is configured to generate the set of frames 416 of 2D ultrasound images. Each of the 2D ultrasound images correspond to ultrasound data acquired at different points along the lateral axis 418 representing one of the frames 416. Additionally or alternatively, the controller circuit 202 may obtain the set of frames of the 2D ultrasound images by accessing the memory 204, and/or a remote system (e.g., server).

At 608, the controller circuit 202 matches the angle and position measurements to each of the frames of the 2D ultrasound images. Optionally, the controller circuit 202 may match the angle and position measurements to each of the frames based on when the measurements and ultrasound data corresponding to the frames were acquired. For example, during the scan the controller circuit 202 may assign timestamps to each of the frames and the angle and position measurements. The timestamps may correspond to a clock value generated by the controller circuit 202. The timestamps represent when the ultrasound data corresponding to each of the frames were acquired by the ultrasound probe 102. Additionally, the timestamps represent when the sensor measurement values were acquired by the inertial measurement circuit 206 of the ultrasound probe 102. The timestamps may be based on the scan performed by the ultrasound imaging system 100. For example, each of the timestamps may represent an amount of time (e.g., milliseconds, seconds, and/or the like) during and/or from the start of the scan. Additionally or alternatively, the timestamp may represent a system clock value of the controller circuit 202.

Based on the timestamp values assigned to the frames and the angle and position measurements, the controller circuit 202 may group the angle and position measurements to a corresponding frame. For example, the controller circuit 202 may assign a first timestamp to an angle and position measurement, which is based on when the sensor measurement values were acquired by the inertial measurement circuit 206. The controller circuit 202 may concurrently assign a second timestamp to a frame based on when the ultrasound probe 102 received the ultrasound data, which was utilized by the controller circuit 202 to generate the frame. The controller circuit 202 may determine that a value of the first timestamp is the same as and/or within a predetermined threshold of a value of the second timestamp. Based on the same and/or similar values of the first and second timestamps the controller circuit 202 may match the angle and positioned measurements of the first timestamp with the frame of the second timestamp.

It may be noted that multiple angle and position measurements may be matched to a single frame. For example, the inertial measurement circuit 206 may acquire sensor measurement values at a rate larger than the acquisition of ultrasound data by the ultrasound probe 102. Based on the changes in acquisition rates, a plurality of angle and position measurements may correspond to a single frame.

For example, the inertial measurement circuit 206 may acquire 100-200 sensor measurement values per second. In various embodiments, due to the rate of the ultrasound data acquired by the ultrasound probe 102 only 20-30 frames of the 2D ultrasound images are captured by the controller circuit 202 per second. Thereby, during the timestamp representing the acquisition of ultrasound data to generate one of the frames 416, the controller circuit 202 may assign timestamp values of at least 5 angle and position measurements. For example, the controller circuit 202 may match at least 5 angle and position measurements to one of the frames.

At 610, the controller circuit 202 identifies frames that includes an organ of interest (OOI). For example, in connection with FIG. 7, the controller circuit 202 may develop a prospect model 702 indicating a likelihood that the frames 416 includes the OOI.

Figure 7:
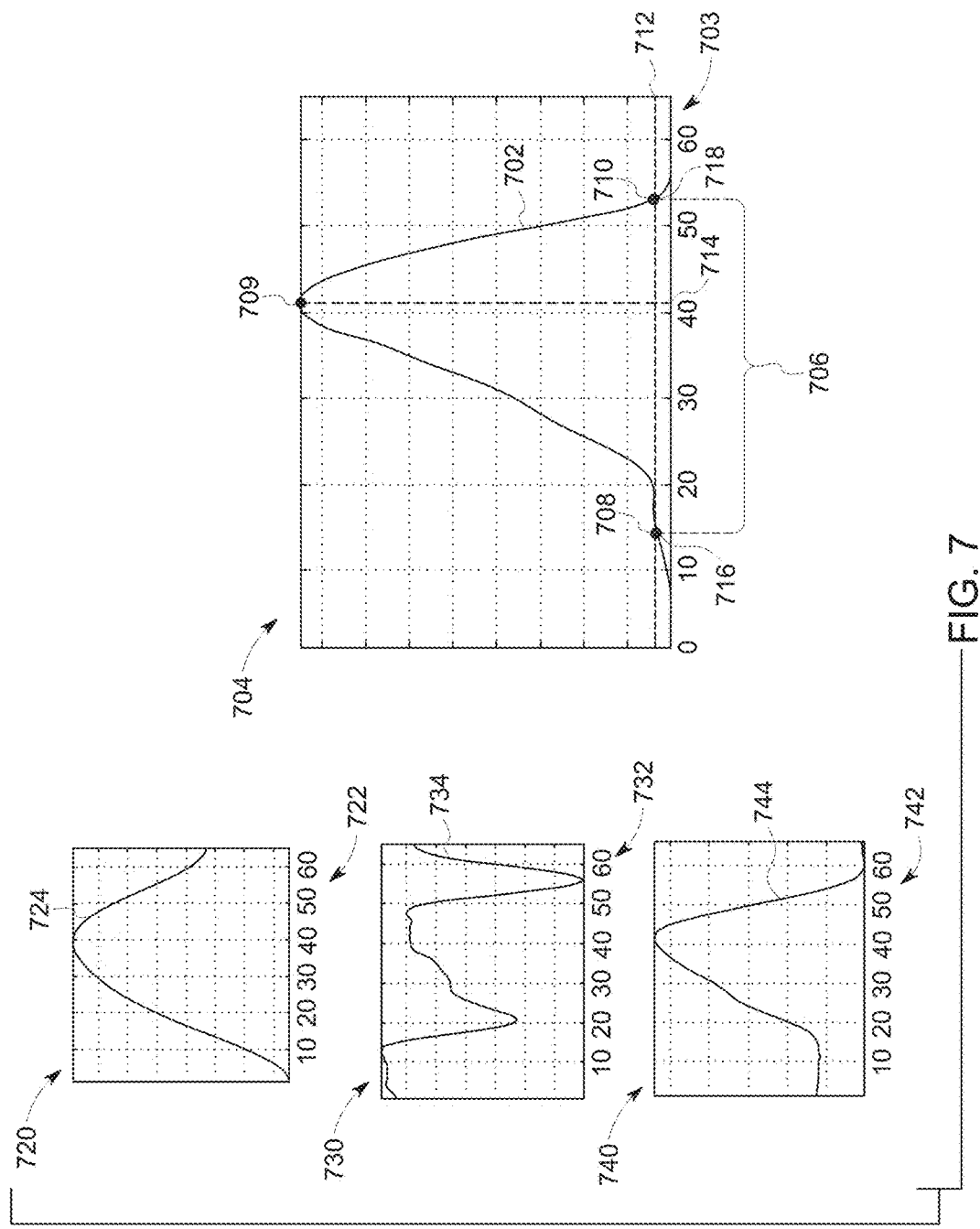
FIG. 7 illustrates a set of graphical illustrations that form a prospect model, in accordance with various embodiments described herein.

FIG. 7 illustrates a set of graphical illustrations 720, 730, 740 that form the prospect model 702, in accordance with various embodiments described herein. The prospect model 702 is plotted along a horizontal axis 703 representing the frames 416 acquired during the scan. The frames 416 are ordered successively based on the timestamps assigned by the controller circuit 202. For example, the number of frames 416 along the horizontal axis 703 represents the frames 416 acquired by the controller circuit 202 during the scan.

The prospect model 702 may be calculated by the controller circuit 202 utilizing a data fusion of separate calculations based on relationship between the pixel values of the frames, the angle and position measurements, and/or the like. The separate calculation are presented by the graphical illustrations 720, 730, 740, which are each plotted along a horizontal axes 722, 732, 742 representing the frames 416. Each of the separate calculations may utilize one or more characteristics of the frames 416 (e.g., pixel intensity, position of the ultrasound probe 102.

The graphical illustration 720 may be based on the tilt angle and positional measurements of the ultrasound probe 102. For example, the controller circuit 202 may combine the tilt angle and acceleration measurements of the ultrasound probe 102 along the z-axis 420 (FIG. 4) utilizing a gradient and complementary filter to generate a curve 724 of the graphical illustration 720.

The graphical illustrations 730 and 740 may be based on pixel information within each of the frames 416. For example, the controller circuit 202 may calculate a first and second series of correlation values 734, 744 based on a relationship between the frames 416. The first series of correlation values 734 are plotted within the graphical illustration 730. The first series of correlation values 734 may represent a cross correlation between successive frames 416 acquired during the scan. For example, the first series of correlation values 734 identify a pixel pattern between adjacent frames 416. The cross correlation represent a series of values for each frame corresponding to a correlation, such as a pattern of pixel values between a pair of adjacent or successive frames 416. The frames 416 that have a higher correlation may correspond to a common structure within each of the higher correlation frames. For example, the common structure may represent the OOI.

The second series of correlation values 744 are plotted within the graphical illustration 740. The second series of correlation values 744 may represent average voxel variations within an area of interest. For example, the controller circuit 202 may identify regions of interest in adjacent frames of the frames 416, and calculate pixel intensity information for the regions of interest. Based on changes in an average pixel intensity within an area of interest in each of the frames 416, the controller circuit 202 may determine a likelihood the region of interest includes the OOI. The area of interest within the frame may correspond to an approximate position of the OOI based on priori information. The priori information may be an approximate position of the OOI based on a plurality of prior scans, such as from clinical trials. For example, the controller circuit 202 may execute a principal component analysis on the priori information to generate an approximate area of the frames 416 that may correspond to the OOI.

In another example, the region of interest may represent the OOI based on a classification model stored in the memory 204. The classification model may correspond to a machine learning algorithm based on a classifier (e.g., random forest classifier) that builds a pixel level classifier model to label and/or assign each pixel of the frames 416 into a plurality of categories or classes (e.g., muscle, fat, background anatomy, OOI). The classification model may determine the classes from a feature space of the pixels based from the various intensities and spatial position of pixels of the frames 416.

Figure 8:
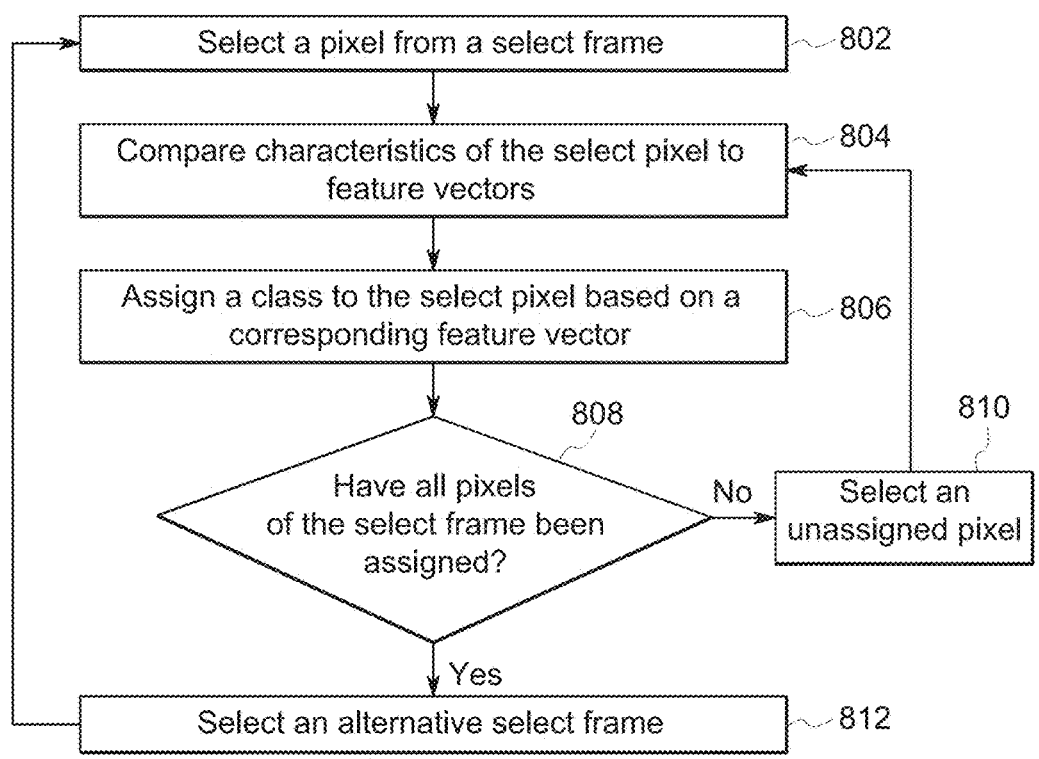
FIG. 8 is a workflow diagram illustrating operational steps of a controller executing a classification model, in accordance with various embodiments described herein.

FIG. 8 illustrates a workflow diagram 800 of the controller circuit 202 for executing a classification model. In various embodiments, certain steps (or operations) of the workflow diagram 800 may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. For example, the controller circuit 202, by executing the classification model, assigns and/or labels the pixels of the ultrasound image into classes corresponding to portions of the OOI. In connection with FIG. 9, the controller circuit 202 determines which pixels of a frame 902 correspond to a background anatomy 912, muscle tissue 914, fat 916, and/or the OOI 910. The controller circuit 202 may assign the pixels based on feature vectors of the classification model corresponding to one or more classes.

Returning to FIG. 8, at 802, the controller circuit 202 selects a pixel of a select frame (e.g., one of the frames 416).

At 804, the controller circuit 202 compares characteristics of the select pixel to feature vectors. For example, the controller circuit 202 may compare an intensity or brightness of the select pixel to feature vectors of the classification model. In another example, the controller circuit 202 may determine a variance kurtosis, skewness, or spatial distribution characteristic of the select pixel by comparing the intensity of the select pixel with adjacent and/or proximate pixels around the select pixel. A number of characteristics of the select pixel compared by the controller circuit 202 may be based on the feature sets included in the feature vectors.

Each feature vector is an n-dimensional vector that includes three or more features of pixels (e.g., mean, variance, kurtosis, skewness, spatial distribution) corresponding to a class (e.g., a background anatomy 912, muscle tissue 914, fat 916, the OOI 910) of pixels of anatomy within an ultrasound image. The feature vectors of the classification model may be generated and/or defined by the controller circuit 202 and/or a remote system based from a plurality of reference ultrasound images. For example, the controller circuit 202 may select pixel blocks from one hundred reference ultrasound images. The select pixel blocks may have a length of five pixels and a width of five pixels. The select pixel blocks may be selected and/or marked by the user to correspond to one of the classes (e.g., muscle, fat, background anatomy, tissue of the OOI). For example, a plurality of pixels within each select pixel block may represent and/or correspond to one of the classes, such as tissue of the OOI. Based on the plurality of pixels within the select pixel blocks, the controller circuit 202 may generate and/or define a feature vector.

For example, the controller circuit 202 may determine feature sets for each pixel within the plurality of pixels of a select pixel block or more than one select pixel block corresponding to the same class. One of the feature sets may be based on an intensity histogram of the reference ultrasound images. For example, the controller circuit 202 may calculate a mean intensity of the plurality of pixels, a variance of the plurality of pixel intensities, a kurtosis or shape of intensity distribution of the plurality of pixels, a skewness of the plurality of pixels, and/or the like. Additionally, one of the feature sets may correspond to a position or spatial feature of the pixels within the select pixel block. For example, a spatial positon with respect to a positon within the reference image (e.g., central location) and a depth with respect to an acquisition depth within the patient. The controller circuit 202 may perform a k-means clustering and/or random forest classification on the feature sets to define feature values that correspond to the class of the select pixel blocks. The controller circuit 202 may define a feature vector corresponding to the class based on the feature values to the classification model.

Additionally or alternatively, the feature vector may be further defined based on a validation analysis. For example, the controller circuit 202 use a k-fold cross validation by subdividing the select pixel blocks with a plurality of pixels for one of the classes into k random parts with (k-1) parts being used by the controller circuit 202 to define the feature vector and the remaining select pixel blocks for testing or validation of the feature vector.

Additionally or alternatively, the controller circuit 202 may further assign each of the plurality of pixels binary codes (e.g., an eight digit binary code). For example, the binary code may be derived by comparing a center pixel value of the select pixel block with the remaining plurality of pixels within the select pixel block.

At 806, the controller circuit 202 may assign a class to the select pixel based on a corresponding feature vector. For example, the controller circuit 202 may determine a candidate feature vector that includes feature sets that are approximately the same and/or within a set threshold to the characteristics of the select pixel based on the comparison at 1003. The controller circuit 202 may assign the class of the candidate feature vector to the select pixel. For example, as shown in 902 in FIG. 9, the controller circuit 202 may assign a background anatomy 912, muscle tissue 914, fat 916, and/or the OOI 910 class to the select pixel.

When the select pixel is assigned a class, the controller circuit 202 may repeat the classification model to the remaining pixels of the select ultrasound image, as shown at 808 and 810 of FIG. 8. When all of the pixels of the controller circuit 202, then at 812, the controller circuit 202 may select an alternative frame (e.g., successive frame, adjacent frame).

Returning to FIG. 7, the controller circuit 202 may combine the curve 724 (e.g., tilt angle), the first series of correlation values 734 (e.g., pixel pattern), and the second series of correlation values 744 (e.g., pixel intensity information) to generate and/or derive the prospect model 702. The vertical axis 704 may represent a value corresponding to a likelihood the frames 416 include the OOI. For example, the controller circuit 202 may compare the prospect model 702 with a predetermined threshold 712. The predetermined threshold 712 may be utilized by the controller circuit 202 to determine a subset 706 of the frames 416 that include the OOI. For example, the frames 416 corresponding to the prospect model 702 above the predetermined threshold 712, between points 708 and 710, is determined by the controller circuit 202 to include the OOI. In another example, the frames 416 corresponding to the prospect model 702 below the predetermined threshold 712 is determined by the controller circuit 202 to not include the OOI.

At 612, the controller circuit 202 selects a primary reference frame 714 representing a center of the OOI. Optionally, the primary reference frame 714 may intersect a center of the OOI, an intermediate position within the OOI, and/or include a cross-section of the OOI. For example, the controller circuit 202 may identify the primary reference frame 714 based on the prospect model 702. The primary reference frame 714 at a center of the OOI may have a higher likelihood relative to the remaining frames 416 since the primary reference frame 714 will include more pixels representing the OOI. The higher likelihood value may correspond to a peak 709 of the prospect model 702. The controller circuit 202 may determine the primary reference frame 714 based on a morphology (e.g., slope, peak, and/or the like) of the prospect model 702. For example, the controller circuit 202 may identify the peak 709 based on changes in slope polarity of the prospect model 702 and/or by comparing values of the prospect model 702 to identify a highest value.

Additionally or alternatively, the controller circuit 202 may identify secondary reference frames 716, 718 based on the prospect model 702. The secondary reference frames 716, 718 may correspond to a different intermediate position of the OOI relative to the primary reference frame 714. Additionally or alternatively, the secondary reference frames 716, 718 may correspond to peripheral edges of the OOI. For example, the secondary reference frame 716 may correspond to a beginning or first of the frames 416 that is determined by the controller circuit 202 to includes the OOI. In another example, the secondary reference frame 718 may correspond to an end or last of the frames 416 that is determined by the controller circuit 202 to include the OOI. The controller circuit 202 may identify the secondary reference frames 716, 718 based on the prospect model 702 with respect to the predetermined threshold 712. For example, the controller circuit 202 may determine that the secondary reference frames 716, 718 are positioned at intersects at the points 708 and 710 of the prospect model 702 with the predetermined threshold 712.

At 614, the controller circuit 202 segments the OOI from the primary reference frame 714. Optionally, as shown at 904 of FIG. 9, the controller circuit 202 may perform a binary mask to partition or isolate pixels corresponding to the OOI 920 from the primary reference frame 714. For example, the controller circuit 202 may execute the classification model stored in the memory 204 to identify the plurality of pixels corresponding to the OOI from the primary reference frame 714. The controller circuit 202 may generate a binary mask based on the identified pixels of the OOI 920 and the remaining pixels of the primary reference frame 714. The controller circuit 202 utilizing the binary mask on the primary reference frame 714, may extract the pixels corresponding to the OOI 920 from the primary reference frame 714.

Figure 9:
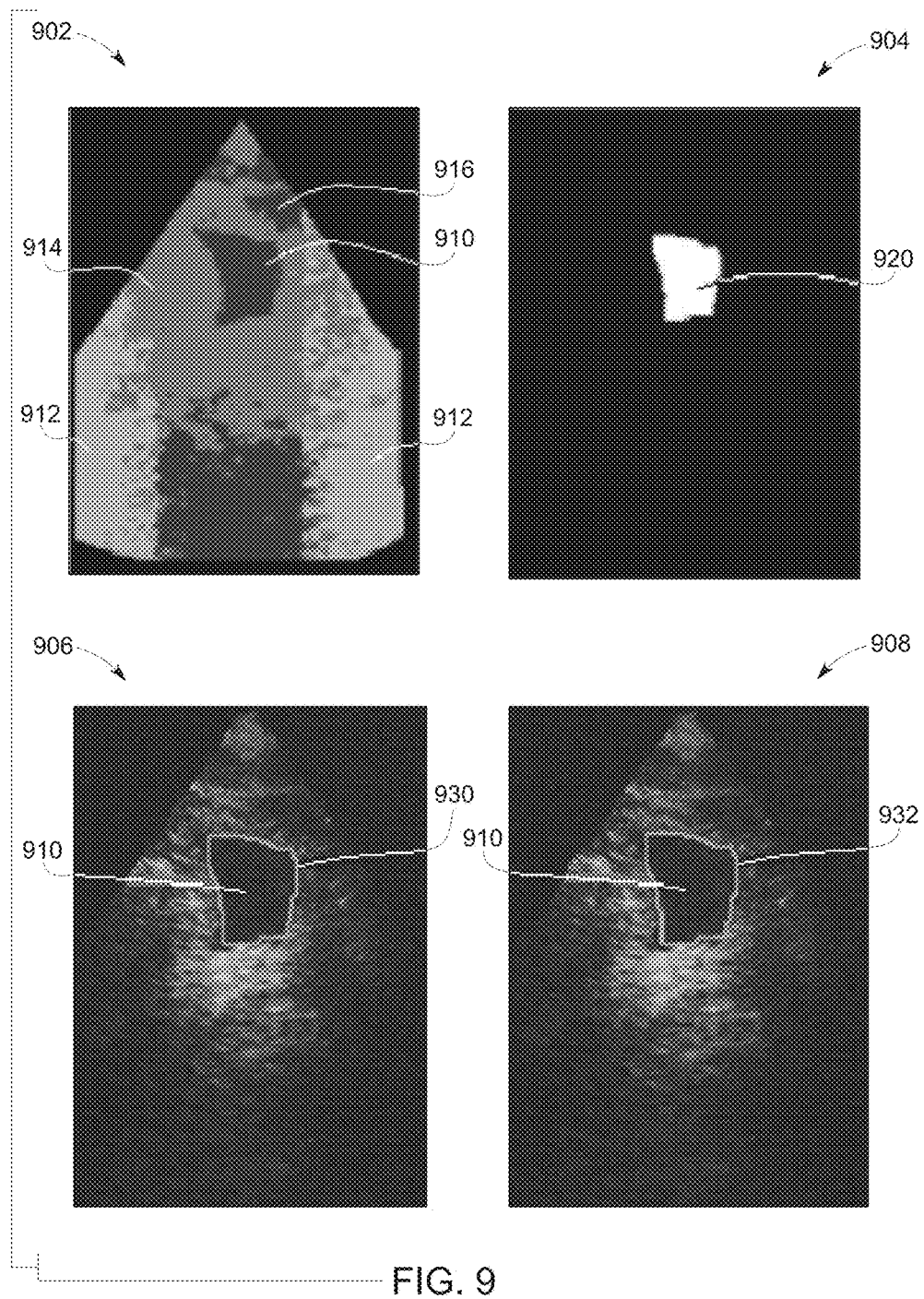
FIG. 9 illustrates a frame of a two dimensional ultrasound image being adjusted during the workflow diagram of FIG. 8 and a contour model, in accordance with various embodiments described herein.

In connection with FIG. 9, the controller circuit 202 may determine a boundary 932 of the OOI 910 by executing a contour model stored in the memory 204 to determine the first boundary of the OOI 910. As shown at 906, the controller circuit 202 may form an initial boundary 930 of the OOI 910. The initial boundary 930 may be determined based on the identified pixels determined from the classification model and/or the binary mask at 904.

As shown at 908, the controller circuit 202 may adjust the initial boundary 930 by executing the contour model stored in the memory 204 to form the boundary 932. The contour model may be similar to the contour model described in in U.S. patent application Ser. No. 14/928,241 entitled "METHOD AND SYSTEM FOR MEASURING A VOLUME FROM AN ULTRASOUND IMAGE," which is incorporated herein by reference in its entirety. The contour model may be based on traditional active contour models (e.g., snakes) with an additional distance regularization term to intrinsically maintain the regularity of a zero level set, the variable $\emptyset$ of Equation 1, while the controller circuit 202 executes the contour model. The distance regularization term may use a double well potential function such that the derived level set evolution has a unique forward and backward diffusion effects. The distance regularization term e issues the address of curve re-initialization and maintains the shape of evolving front. Additionally, the contour model may include an external energy term defined by equation 1. The external energy term may be based on image gradients, shown as the variable F, to drive a motion of the level curve to desired locations corresponding to the boundary of the OOI 910. The variable A of Equation 1 correspond to an area of the OOI 910, and the variable $d_p$ is the potential function.

$$\frac{\partial \phi}{\partial t} = \mu div(d_p(|\nabla \phi|)\nabla \phi) + F|\nabla \phi| + A \cdot \nabla \phi \quad \text{Equation 1}$$

At 616, the controller circuit 202 selects a candidate shape for the OOI 910 based on a characteristic of interest in the primary reference frame 714. The candidate shape may be a 3D representative of the OOI 910 stored in the memory 204. For example, the memory 204 may include a plurality of candidate shapes. The controller circuit 202 may select a set of candidate shapes from the plurality based on the scan performed by the system 100.

The characteristic of interest may correspond to a dimensional feature of the OOI 910 of the primary reference frame 714. For example, the characteristic of interest may be the boundary 932 of the OOI 910, ratio of dimensions (e.g., length, width) of the OOI 910, the binary mask of the OOI 920, tilt angle of the primary reference frame 714, and/or the like. Based on the characteristic of interest, the controller circuit 202 may select a candidate shape from the set of candidate shapes representative of the OOI 910. For example, the set of candidate shapes may be a trapezoidal shape, a cuboid, and/or an ellipsoid. The controller circuit 202 may calculate shape matching values for each of the set of candidate shapes based on the characteristic of interest of the primary reference frame 714. The shape matching values represent a likelihood the OOI 910 of the primary reference frame 714 corresponds to one of the set of candidate shapes.

For example, the controller circuit 202 may calculate a shape matching value for the trapezoidal shape, the cuboid, and the ellipsoid based on the characteristic of interest. One of the shape matching values may correspond to the controller circuit 202 calculating a difference in a widths of the boundary 932, such as a width of the boundary 932 at opposing ends of the OOI 910, for the trapezoidal shape. The larger the difference in the widths of the boundary 932, the higher the shape matching value calculated by the controller circuit 202 for the trapezoidal shape. In another example, the controller circuit 202 may execute a line fit at a peripheral edge of the boundary 932 (e.g., bottom edge) to determine the shape matching value for the cuboid. The controller circuit 202 may determine that the more parallel the line fit is the higher the shape matching value is for the cuboid. In another example, the controller circuit 202 may calculate an elliptical error fit of a peripheral edge of the boundary 932 (e.g., bottom edge) to determine the shape matching value for the ellipsoid. The controller circuit 202 may determine that the smaller the elliptical error is the higher the shape matching value is for the ellipsoid. The controller circuit 202 may select one of the candidate shapes from the set of candidate shapes that has the highest shape matching value.

At 618, the controller circuit 202 adjusts the candidate shape based on the secondary reference frames 716, 718 to form a resultant shape for the OOI 910. Additionally or alternatively, the controller circuit 202 may adjust the candidate shape based on the set of frames 416 to the resultant shape for the OOI 910. For example, the controller circuit 202 may execute an active contour model (e.g., real-time contour tracking library) stored in the memory 204. The active contour model may adjust a size and/or contour of the candidate shape based on characteristics of interest in the secondary reference frames 716, 718. Optionally, the active contour model may deform the shape of the candidate shape to match, align, and/or the like the characteristics of interest of the secondary reference frames 716, 718.

For example, when executing the active contour model the controller circuit 202 may adjust the candidate shape based on a tilt angle of the secondary reference frames 716, 718 by estimating a 3D position of the pixels of the secondary reference frames 716, 718 and adjust a point of the candidate shape to the 3D position. The 3D position may be determined by the controller circuit 202 based on Equation 2 shown below. The variable $$\left(\frac{S}{U}\right)T$$

is a 4×4 transformation matrix that represents the co-ordinate transformation between the secondary reference frames 716, 718 based on the inertial measurement circuit 206. Optionally, the variable $$\left(\frac{S}{U}\right)T$$

may be an identity matrix. The variable $$\left(\frac{T}{S}\right)T$$

is a 4×4 transformation matrix representing the co-ordinate transformation between the inertial measurement circuit 206 and the transducer array 106. The controller circuit 202 may utilize the positon and angle measurements corresponding to the secondary reference frames 716, 718 is utilized to define the 4×4 transformation.

$$\left(\frac{T}{S}\right)T.$$

The variable $x_U$ represents a position of an image pixel within the secondary reference frame 716, 718 (e.g., $x_U^i$, $y_U^i$, 0,1) and $X_T$ represents a position of the image pixel relative to the transducer array 106 and/or patient (e.g., $x_T^i$, $y_T^i$, $z_T^i$, 1).

$$x_T = \left(\frac{T}{S}\right)T \cdot \left(\frac{S}{U}\right)T \cdot x_U \qquad \text{Equation 2}$$

In another example, when executing the active contour model the controller circuit 202 may adjust peripheral edges of the candidate shape by deforming a position and/or curve of the peripheral edge to match the characteristic of interest (e.g., boundary, binary mask, and/or the like) of the secondary reference frames 716, 718.

Figure 10:
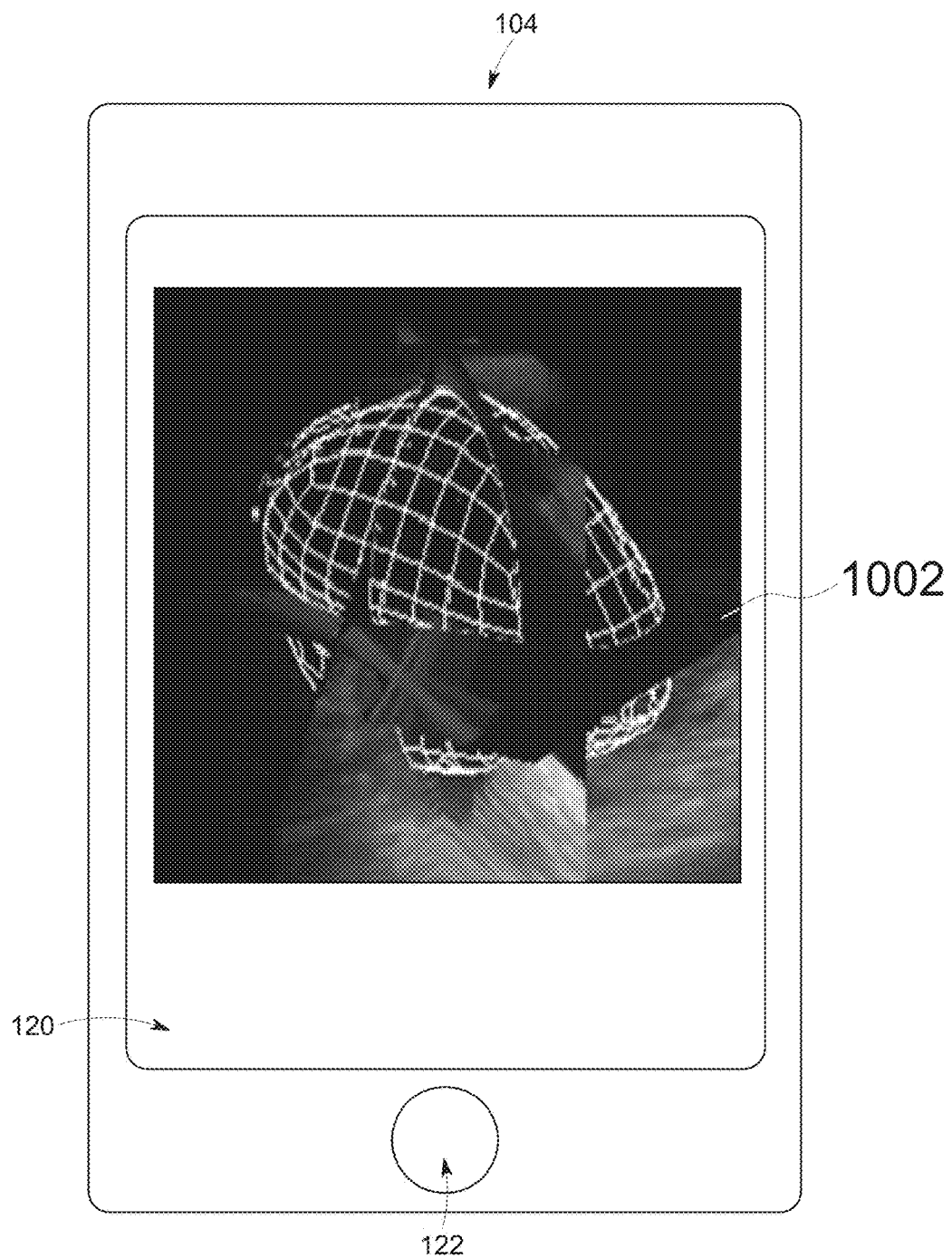
FIG. 10 illustrates a three dimensional image of an organ of interest, in accordance with various embodiment described herein.

At 620, the touchscreen display 120 displays the adjusted candidate shape of the OOI 910. In connection with FIG. 10, the controller circuit 202 may instruct the touchscreen display 120 of the portable host system 104 to display a 3D image 1002 representing the OOI 910. FIG. 10 illustrates the 3D image 1002 of the OOI 910. The 3D image 1002 may represent the adjusted candidate shape of the OOI 910.

Additionally or alternatively, the controller circuit 202 may adjust the 3D image 1002 based on user adjustments by the user received from the touchscreen display 120. For example, the user may select a user selectable element shown concurrently with the 3D image 1002 of the OOI 910. The user selectable element may represent an adjustment tool executed by the controller circuit 202. The controller circuit 202 may be configured to apply a plurality of orthogonal planes that extend through the 3D image 1002 when the adjustment tool is selected. For example, the controller circuit 202 may add a first orthogonal plane extending through the 3D image 1002, a second orthogonal plane, and a third orthogonal plane. Each of the orthogonal planes may be perpendicular with respect to each other extending within the 3D image 1002. Optionally, the first orthogonal plane may represent a sagittal plane, the second orthogonal plane may represent a transverse plane, and the third orthogonal plane may represent a coronal plane. The user may adjust the 3D image 1002 along the orthogonal planes by adjusting a peripheral boundary and/or position of the 3D image 1002 with respect to the 3D image 1002. For example, the controller circuit 202 may add calipers similar to and/or the same as the calipers described in in U.S. patent application Ser. No. 14/928,241 entitled "METHOD AND SYSTEM FOR MEASURING A VOLUME FROM AN ULTRASOUND IMAGE," which is incorporated herein by reference in its entirety, to adjust the 3D image 1002. Optionally, based on the adjusted portion of the 3D image 1002 by the user, the controller circuit 202 may adjust the remaining 3D image utilizing the active contour model described at 618.

At 622, the touchscreen display 120 detects a user select position to measure a volume of the OOI 910. For example, the controller circuit 202 may detect a selection of a graphical icon corresponding to an instruction by the user to measure the volume of the OOI 910.

At 624, the controller circuit 202 calculates a volume of the OOI 910. For example, the controller circuit 202 may sum and/or add the voxels of the 3D image 1002 to determine a volume of the OOI 910.

At 626, the touchscreen display 120 displays the volume of the OOI 910. For example, the controller circuit 202 may instruct the touchscreen display 120 to display a numeral and/or graphical value representing the volume of the OOI 910.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method comprising:
obtaining a set of frames of 2D ultrasound images;
using one or more processors to:
develop a prospect model indicating a likelihood that frames within the set include an organ of interest (OOI), wherein the prospect model comprises a cross correlation between successive frames in the set of frames;
identify a primary reference frame and a secondary reference frame from the set of the frames based on the prospect model, wherein the second reference frame was acquired with the ultrasound probe at a different tilt angle than the primary reference frame;
determine a characteristic of interest in the primary reference frame;
select a candidate shape for the OOI based on the characteristic of interest in the primary reference frame, wherein the candidate shape is a 3D representation of the OOI, and wherein the candidate shape is selected from a plurality of candidate shapes stored in a memory;
adjust the candidate shape based on the secondary reference frame to form a resultant shape for the OOI;
calculate a volume of the OOI using the resultant shape; and
display the volume of the OOI.

2. The method of claim 1, wherein the identify operation includes identifying, from the set of frames, an ultrasound image that intersects a center of the OOI, the ultrasound image representing the primary reference frame.

3. The method of claim 1, wherein the develop operation includes identifying a pixel pattern between adjacent frames in the set of frames and deriving the prospect model based on the pixel pattern.

4. The method of claim 1, wherein the develop operation includes identifying regions of interest in adjacent frames in the set of frames, calculating pixel intensity information for the regions of interest, and deriving the prospect model based on the pixel intensity information.

5. The method of claim 1, wherein the develop operation includes determining tilt angle information regarding for at least a portion of the set of frames, and deriving the prospect model based on the tilt angle information.

6. The method of claim 1, wherein the characteristic of interest represents at least one of a boundary of the OOI or a ratio of dimensions for the OOI.

7. The method of claim 1, wherein the adjust operation includes adjusting at least one of a size or contour of the candidate shape based on characteristic of interest in the secondary reference frame.

8. The method of claim 1, wherein the OOI is a bladder, a stomach, a kidney or a liver.

9. A mobile ultrasound imaging system comprising:
a portable host system having one or more processors and a memory for storing a plurality of applications that include corresponding programmed instructions, wherein when a select application is activated the one or more processors execute programmed instructions of the select application by performing the following operations:
obtain a set of frames of 2D ultrasound images;
develop a prospect model indicating a likelihood that frames within the set include an organ of interest (OOI), wherein the prospect model comprises a cross correlation between successive frames in the set of frames;
identify a primary reference frame and a secondary reference frame from the set of the frames based on the prospect model, wherein the second reference frame was acquired with the ultrasound probe at a different tilt angle than the primary reference frame;
determine a characteristic of interest in the primary reference frame;
select a candidate shape for the OOI based on the characteristic of interest in the primary reference frame, wherein the candidate shape is a 3D representation of the OOI, and wherein the candidate shape is selected from a plurality of candidate shapes stored in the memory;
adjust the candidate shape based on the secondary reference frame to form a resultant shape for the OOI;
calculate a volume of the OOI using the resultant shape; and
display the volume of the OOI.

10. The mobile ultrasound imaging system of claim 9, wherein the identify operation includes identifying, from the set of frames, an ultrasound image that intersects a center of the OOI, the ultrasound image representing the primary reference frame.

11. The mobile ultrasound imaging system of claim 9, wherein the develop operation includes identifying a pixel pattern between adjacent frames in the set of frames and deriving the prospect model based on the pixel pattern.

12. The mobile ultrasound imaging system of claim 9, wherein the develop operation includes identifying regions of interest in adjacent frames in the set of frames, calculating pixel intensity information for the regions of interest, and deriving the prospect model based on the pixel intensity information.

13. The mobile ultrasound imaging system of claim 9, wherein the develop operation includes determining tilt angle information regarding for at least a portion of the set of frames, and deriving the prospect model based on the tilt angle information.

14. The mobile ultrasound imaging system of claim 9, wherein the characteristic of interest represents at least one of a boundary of the OOI or a ratio of dimensions for the OOI.

15. The mobile ultrasound imaging system of claim 9, wherein the adjust operation includes adjusting at least one of a size or contour of the candidate shape based on characteristic of interest in the secondary reference frame.

16. A tangible and non-transitory computer readable medium comprising one or more programmed instructions configured to direct one or more processors to:
obtain a set of frames of 2D ultrasound images;
develop a prospect model indicating a likelihood that frames within the set include an organ of interest (OOI), wherein the prospect model comprises a cross correlation between successive frames in the set of frames;
identify a primary reference frame and a secondary reference frame from the set of the frames based on the prospect model, wherein the second reference frame was acquired with the ultrasound probe at a different tilt angle than the primary reference frame;
determine a characteristic of interest in the primary reference frame;

select a candidate shape for the OOI based on the characteristic of interest in the primary reference frame, wherein the candidate shape is a 3D representation of the OOI, and wherein the candidate shape is selected from a plurality of candidate shapes stored in a memory;

adjust the candidate shape based on the secondary reference frame to form a resultant shape for the OOI;

calculate a volume of the OOI using the resultant shape; and displaying the volume of the OOI.

17. The method of claim 1, wherein the candidate shape is selected from the group consisting of a trapezoidal shape, a cuboid, and an ellipsoid.

18. The mobile ultrasound imaging system of claim 9, wherein the candidate shape is selected from the group consisting of a trapezoidal shape, a cuboid, and an ellipsoid.

* * * * *